United States Patent
Ditrich et al.

(10) Patent No.: US 11,866,443 B2
(45) Date of Patent: Jan. 9, 2024

(54) METHOD FOR SEPARATING OPTICALLY ACTIVE HYDROXY CINEOLE DERIVATIVES

(71) Applicant: BASF Agro B.V., Arnhem (NL)

(72) Inventors: Klaus Ditrich, Ludwigshafen (DE); Michael Rack, Ludwigshafen (DE); Stefan Benson, Ludwigshafen (DE); Roland Goetz, Ludwigshafen (DE); Helmut Kraus, Research Triangle Park, NC (US)

(73) Assignee: BASF AGRO B.V., Arnhem (NL)

( * ) Notice: Subject to any disclaimer, the term of this patent is extended or adjusted under 35 U.S.C. 154(b) by 0 days.

(21) Appl. No.: 16/614,400

(22) PCT Filed: May 9, 2018

(86) PCT No.: PCT/EP2018/062042
§ 371 (c)(1),
(2) Date: Nov. 18, 2019

(87) PCT Pub. No.: WO2018/210663
PCT Pub. Date: Nov. 22, 2018

(65) Prior Publication Data
US 2020/0148697 A1    May 14, 2020

(30) Foreign Application Priority Data
May 19, 2017  (EP) .................... 17171875

(51) Int. Cl.
C07D 493/08  (2006.01)
C07B 57/00   (2006.01)

(52) U.S. Cl.
CPC ............ C07D 493/08 (2013.01); C07B 57/00 (2013.01); *C07B 2200/07* (2013.01)

(58) Field of Classification Search
CPC .................................................. C07D 493/08
See application file for complete search history.

(56) References Cited

U.S. PATENT DOCUMENTS 4,487,945 A    12/1984    Payne

FOREIGN PATENT DOCUMENTS

EP    0081892 A2    6/1983

OTHER PUBLICATIONS

Stahl "Handbook of Pharmaceutical Salts: Properties Selection and Use" Verlag Helvetica Chimica Acta: 2002, pp. 191-211.*
University of Pittsburgh Lecture Notes of George C. Bandik, Online "http://www.pitt.edu/~bandik/organicweb/recrystallization.html" Mar. 29, 1999 accessed Mar. 18, 2021.*
Ohloff, "2. Absolute Konfiguration von Terpinenol(4)Helv. Chim. Acta 1965, 48, 10-28.*
Liu "Stereochemistry of Microbiological Hydroxylations of 1,4-Cineole" J. Org. Chem. 1988, 53, 5700-5704.*
Gérard Coquerel "Preferential Crystallization" in Novel Optical Resolution Technologies Top Curr Chem (2007) 269: 1-51 Springer-Verlag Berlin Heidelberg 2006.*
Konuki "Enantiomeric purity enrichment of (R)-tetrahydrothiophene-3-ol sulfonyl derivatives by crystallization" Tetrahedron: Asymmetry 25 (2014) 1581-1589.*
European Search Report for EP Patent Application No. 17171875.2, dated Aug. 21, 2017, 4 pages.
Guan, et al., "The First Preparation of Enantiopure I-Methyl-7-oxabicyclo[2.2.I]heptan-2-one, A Versatile Chiral Building Block for Terpenoids", Chirality, vol. 17, Issue 2, Jan. 1, 2005, pp. 113-118.
International Search Report for PCT Patent Application No. PCT/EP2018/062042, dated Jul. 12, 2018, 4 pages.
Liu, et al., "Stereospecific Transformation of Terpinen-4-ol to Dihydropinol", Synthetic Communications, vol. 26, Issue 14, 1996, pp. 2731-2735.
Pálovics, et al., "Separation of the Mixtures of Chiral Compounds by Crystallization", Advances in Crystallisation Processes, Apr. 2012, pp. 1-38.
Secor,"Resolution of Optical Isomers by Crystallization Procedures", Chemical Reviews, vol. 63, Issue 3, Jun. 18, 1962, pp. 297-309.
Vogel, et al., "Derivatives of 7-oxabicyclo[2.2.1]Heptane in Nature and as Useful Synthetic Intermediates", Tetrahedron, vol. 55, Issue 48, Nov. 26, 1999, pp. 13521-13642.

\* cited by examiner

*Primary Examiner* — David K O'Dell
(74) *Attorney, Agent, or Firm* — MARSHALL, GERSTEIN & BORUN LLP

(57) ABSTRACT

The present invention relates to a method for separating an optically active hydroxy cineole derivatives by lixiviation and crystallization and enantiomerically pure optically active hydroxy cineole derivatives of purity greater than 99.5% that have been prepared by this process. The present invention further relates to use of the desired enantiomer having enantiomeric excess of at least 99.5% ee as prepared according to the present invention, for the synthesis of enantiomerically pure 7-oxabicyclo[2.2.1]heptane derivatives.

8 Claims, No Drawings

METHOD FOR SEPARATING OPTICALLY ACTIVE HYDROXY CINEOLE DERIVATIVES

This application is a National Stage application of International Application No. PCT/EP2018/062042, filed May 9, 2018. This application also claims priority under 35 U.S.C. § 119 to European Patent Application No. 17171875.2, filed May 19, 2017.

FIELD OF THE INVENTION

The present invention relates to a method for separating optically active hydroxy cineole derivatives by lixiviation and crystallization and enantiomerically pure optically active hydroxy cineole derivatives of purity greater than 99.5% that have been prepared by this method.

The present invention further relates to use of the desired enantiomer having enantiomeric excess of at least 99.5% ee as prepared according to the present invention, for the synthesis of enantiomerically pure 7-oxabicyclo[2.2.1]heptane derivatives.

BACKGROUND OF THE INVENTION

Cinmethylin is a herbicide which inhibits tyrosine metabolism and such prevents the plant from producing plastoquinones and tocopherols. Cinmethylin is racemic (±)-2-exo-(o-methyl benzyl ether) of 1,4-cineole. It was introduced as a racemate by Shell in 1989.

2-Hydroxy-1,4-cineole is a key synthetic intermediate and it may be made by the epoxidation of 1,4-terpinen-4-ol followed by acid catalyzed rearrangement. As the epoxidation and acid catalyzed rearrangement occurs in a stereoselective manner, the final product, cinmethylin, is obtained in a non-racemic form when the starting material is non-racemic.

There is always a loss of precious material during the optical resolution of the specific enantiomer. To avoid losses of precious material, it is economic to do a racemate resolution in an early phase of a multi-step synthesis.

It is well-known from the literature (Ref: U.S. Pat. No. 4,487,945; column 8, paragraph 15-25) that enantiomers of cinmethylin show differences in herbicidal activity. The enantiomeric excess plays a very important role in herbicidal activity.

Various methods for separation of optically active enantiomers of organic racemates have been heretofore proposed. Methods based on crystallization using physico-chemical means have been regarded as more advantageous over chemical or biological methods, as the former methods require no expensive reagent for resolution and can be carried out economically on an industrial scale.

Few methods for optical resolution of organic racemates using physico-chemical resolutions have been patented, but these methods have been all based merely on experiments and not on a theory or generalization derived from the experiments.

The relation between the applicability of resolution methods based on the crystallization and the constitution of organic racemates is not clearly predictable and must apparently be checked experimentally case by case [Chem. Rev. 3, 297 (1963)].

A basis for controlling the optical resolution utilizing crystallization is not clearly predictable. When the degree of supersaturation of an organic racemate is high, the resolution cannot, in general, be carried out successfully. In fact, it has been recommended that the resolution should be carried out below a certain limit. However, such limit is not clearly predictable because the basis of such a limit has not been elucidated. Therefore, such a limit for an individual organic racemate must apparently be experimentally determined case by case.

Further, the existing processes for preparation of enantioenriched hydroxy cineol derivatives generally proceed with poor yields, and the optical purity is still not satisfactory either. Thus, there is a need to develop an efficient method for preparing optically active hydroxy-1,4-cineole derivatives with excellent enantiomeric excess without compromising good yield.

Therefore, there is a need to investigate about the possibility to resolve one enantiomer of terpinen-4-ol or hydroxycineol by lixiviation and crystallization and eliminating the use of expensive reagents which are generally used in chemical or biological methods.

OBJECTIVES OF THE INVENTION

The main objective of the invention is to provide a method for separating the optically active hydroxy cineole derivatives by the enantioselective lixiviation and crystallization resolution with an excellent enantiomeric excess without compromising yield.

Another objective of the invention is to provide a simple and efficient method for separating the optically active hydroxy cineole derivatives by successive seeding of crystals of the desired optical enantiomer to an enriched enantiomeric excess of it.

Another object of the invention is to provide a method for a truly chiral resolution by separation, which can be economically and efficiently carried out on an industrial scale in a readily controllable and stable manner.

Still another objective of the invention is to provide enantiomerically pure hydroxy cineole derivatives with enantiomeric excess of greater than 99.5% purity.

SUMMARY OF THE INVENTION

It has now been found that, surprisingly, optically active hydroxy cineole derivatives of the formulae (I-R) and (I-S) can be obtained from an enantiomer mixture by using at least one non-polar solvent enantioselectively by lixiviation and crystallization resolution with excellent enantiomeric excess without compromising yield. After separating the desired enantiomer, the remaining mixture contains the racemate and the same can be recycled in the process. Thus, the loss of the precious material is eliminated. Direct enantiomer separation, without the need for resolving agents, has been achieved by the present invention. A seeding of a supersaturated solution of the racemate with a desired single enantiomer, under controlled conditions increases the enantiomeric excess of the desired enantiomer. The optically active enantiomer so obtained has an enantiomeric excess of at least 99.5% ee. Further, said optically active cineole derivative with enantiomeric excess greater than 99.5% can be used to prepare optically active 7-oxabicyclo[2.2.1]heptane derivatives.

Accordingly, in one embodiment, the presently claimed invention is directed to a method for separating an optically active hydroxy cineole derivative of formula (I-R),

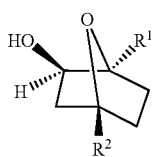

formula (I-R)

or an optically active hydroxy cineole derivative of formula (I-S),

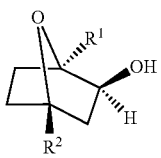

formula (I-S)

wherein
  R¹ is selected from hydrogen and unsubstituted or substituted alkyl and
  R² is selected from hydrogen and unsubstituted or substituted alkyl;
from a mixture comprising the enantiomers of formula (I-R) and formula (I-S),
comprising the steps of:
  i) Providing a suspension comprising a mixture of the enantiomers of formula (I-R) and formula (I-S), wherein the desired enantiomer is present in the mixture in an amount of ≥51 to ≤95 wt.-%, related to the sum of the enantiomers of the mixture, in at least one non-polar solvent;
  ii) Stirring the suspension obtained in step (i) at a temperature in the range of ≥10° C. to reflux temperature of the non-polar solvent; and
  iii) Isolating the crystals of the desired enantiomer obtained in step (ii).

Essentially the desired enantiomer is present in the mixture in an amount of ≥51- to ≤95wt.-%, related to the sum of the enantiomers of the mixture.

In another embodiment of the presently claimed invention, said method further comprising adding seed crystals of the desired enantiomer in step (ii).

The term "seed" crystals denotes a small piece of single crystal/polycrystal of the desired enantiomer from which a large crystal of the same enantiomer typically is to be grown.

In another embodiment of the presently claimed invention, R¹ is selected from hydrogen and $C_1$-$C_6$-alkyl; wherein alkyl is straight-chain or branched, unsubstituted or substituted with 1, 2, 3, 4 or 5 substituents selected from the group consisting of F, Cl, Br, I, CN, $NO_2$, methyl, phenyl and benzyl; and R² is selected from hydrogen and $C_1$-$C_6$-alkyl; wherein alkyl is straight-chain or branched, unsubstituted or substituted with 1, 2, 3, 4 or 5 substituents selected from the group consisting of F, Cl, Br, I, CN, $NO_2$, methyl, phenyl and benzyl.

The term "straight-chain" denotes a chain of atoms with no side chain attached to it.

The term "branched" denotes a chain of atoms with one or more side chains attached to it. Branching occurs by the replacement of a substituent, e.g. a hydrogen atom, with a covalently bonded alkyl radical.

"Alkyl" denotes a moiety constituted solely of atoms of carbon and a hydrogen.

In another embodiment of the presently claimed invention, R¹ is methyl and R² is isopropyl.

In another embodiment of the presently claimed invention, the desired enantiomer is either the optically active hydroxy cineole derivative of formula (I-R) or the optically active hydroxy cineole derivative of formula (I-S).

In another embodiment of the presently claimed invention, in step (ii) the suspension is stirred at a temperature in the range of ≥10 to ≤120° C., preferably ≥20 to ≤115° C.

In another embodiment of the presently claimed invention, in step (iii) the isolation of the crystals of the desired enantiomer is carried out at temperature in the range of ≥−10 to ≤30° C., preferably ≥10 to ≤25° C.

In another embodiment of the presently claimed invention, in step (iii) the desired enantiomer is isolated by a method selected from the group consisting of filtration or evaporation.

In another embodiment of the presently claimed invention, in step (iii) the desired enantiomer as isolated has enantiomeric excess of at least 99.0% ee, preferably 99.5% ee, for example >99.9% ee.

In another embodiment of the presently claimed invention, in step (i) the non-polar solvent is a hydrocarbon.

In another embodiment of the presently claimed invention, in step (i) the non-polar solvent is a hydrocarbon having polarity index of ≥0.0 to ≤2.5.

In another embodiment of the presently claimed invention, the hydrocarbon is selected from the group consisting of petroleum ether, pentane, cyclopentane, hexane, cyclohexane, heptane, n-octane, iso-octane, cyclooctane, benzene, xylene and toluene.

Accordingly, in another embodiment, the presently claimed invention is directed to use of the desired enantiomer having enantiomeric excess of at least 99.5% ee as prepared according to the present invention, for the synthesis of enantiomerically pure 7-oxabicyclo[2.2.1]heptane derivatives.

In another embodiment of the presently claimed invention, the mixture of enantiomers of formula (I-R) and formula (I-S) is prepared by a process comprising the steps of:
  (iv) epoxidation of a terpinenol derivative of formula II

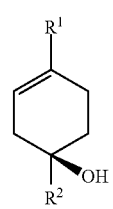

Formula (II)

wherein
  R¹ is selected from hydrogen and unsubstituted or substituted alkyl and
  R² is selected from hydrogen and unsubstituted or substituted alkyl;
in the presence of at least one metal to obtain an epoxide of formula (III);

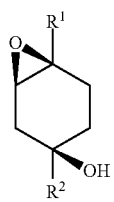

Formula (III)

wherein $R^1$ and $R^2$ are defined as above,
and
(v) subjecting the epoxide of formula (III) to at least one acid.

In another embodiment of the presently claimed invention, $R^1$ is selected from hydrogen and $C_1$-$C_6$-alkyl; wherein alkyl is straight-chain or branched, unsubstituted or substituted with 1, 2, 3, 4 or 5 substituents selected from the group consisting of F, Cl, Br, I, CN, $NO_2$, methyl, phenyl and benzyl; and $R^2$ is selected from hydrogen and $C_1$-$C_6$-alkyl; wherein alkyl is straight-chain or branched, unsubstituted or substituted with 1, 2, 3, 4 or 5 substituents selected from the group consisting of F, Cl, Br, I, CN, $NO_2$, methyl, phenyl and benzyl;

DETAILED DESCRIPTION OF THE INVENTION

For the purposes of promoting an understanding of the principles of the invention, a specific language will be used to describe exemplary embodiments of the present invention. It will nevertheless be understood that no limitation of the scope of the invention is thereby intended. The invention includes any alterations and further modifications in the described methods and described optically active compounds of the principles of the invention which would normally occur to one skilled in the art to which the invention relates.

A racemate is optically inactive, meaning that there is no net rotation of plane-polarized light. Although the two enantiomers rotate plane-polarized light in opposite directions, the rotations cancel because they are present in equal amounts.

In contrast to the two pure enantiomers, which have identical physical properties except for the direction of rotation of plane-polarized light, a racemate sometimes has different properties from either of the pure enantiomers. Different melting points are most common, but different solubilities and boiling points are also possible.

Preparation of enantiopure (ee~100%) compounds is one of the most important aims both for industrial practice and research. Actually, the resolution of racemic compounds (1:1 mixture of molecules having mirror-imagine relationship) still remains the most common method for producing pure enantiomers on a large scale. In these cases, the enantiomeric mixtures or a sort of their derivatives are separated directly. This separation is based on the fact that the enantiomeric ratio in the crystallized phase differs from the initial composition. In this way, obtaining pure enantiomers requires one or more crystallizations.

At the same time, there are some enantiomeric mixtures having racemate properties which show conglomerate behaviour during its purification by fractionated precipitation. Always the enantiomeric excess is crystallized independently from the starting isomeric composition. This is explained by the kinetic crystallization of the enantiomeric excess. Consequently, if the enantiomeric purity obtained after recrystallization or by other partial crystallization (as the result of splitting between the two phases) is plotted against the initial enantiomeric composition, either racemate or conglomerate behaviour is expected, or a conglomerate is obtained.

In the entrainment procedure, the conditions described below suffice in practice to achieve some separation of the enantiomers. Firstly, a saturated solution of the desired enantiomer of hydroxy cineol derivatives is provided at a given temperature. Suitable solvents for the procedure include hydrocarbons. Incorporation of a suitable solvent having polarity index of $\geq 0.0$ to $\leq 2.5$ is also beneficial and allows more efficient enantiomer crystallization.

The term "Lixiviation" means the process of separating soluble from insoluble substances by dissolving the former in water or some other solvent.

According to the present invention, there is provided a method for separating an optically active hydroxy cineole derivative of formula (I-R) or formula (I-S), from a mixture comprising the enantiomers of formula (I-R) and (I-S). Typically, the mixture of the enantiomers of formula (I-R) and formula (I-S), wherein the desired enantiomer is present in the mixture in an amount of $\geq 51$ to $\leq 95$ wt.-%, related to the sum of the enantiomers of the mixture. The mixture of the enantiomers is suspended in at least one non-polar solvent. The suspension is stirred at a temperature in the range of $\geq 10°$ C. to reflux temperature of the non-polar solvent. The crystals of the desired enantiomer are isolated.

The method further comprising adding seed crystals of the desired enantiomer in either suspension or solution to increase enantiomeric excess of the desired enantiomer.

Typically, the suspension is stirred at a temperature in the range of $\geq 10$ to $\leq 120°$ C., preferably at $\geq 20$ to $\leq 115°$ C.

Typically, the isolation of the crystals of the desired enantiomer is carried out at temperature in the range of $\geq -10$ to $\leq 30°$ C., preferably at $\geq 10$ to $\leq 25°$ C.

According to the invention, an amount of racemate from the mixture comprising the enantiomer of formula (I-R) and the enantiomer of formula (I-S) is dissolved in the solvent and leaves behind the desired enantiomer which is isolated. The supersaturated suspension can be seeded with crystals of the desired enantiomer to increase the enantiomeric excess.

Accordingly, a supersaturated solution of the hydroxy cineol derivatives may be entrained by seeding with crystals of the single enantiomer to grow larger crystals having an excess of the enantiomer seeded, and leaving the opposite enantiomer or racemate enriched in the mother liquors. In order to make such an entrainment crystallisation procedure useful for the production of single enantiomer hydroxy cineol derivatives it is desirable that the optically-enriched hydroxy cineol derivatives obtained can be raised in enantiomeric purity through recrystallisation. Nonetheless the overall procedure is a resolution leaving an issue of utilisation of the wrong enantiomer. If it could be racemized or the configuration inverted, then all material could in principle be directed to the required isomer.

An amount of the desired enantiomer from the mixture comprising the enantiomers of formula (I-R) and the enantiomer of formula (I-S) is dissolved in the solvent by warming to effect complete dissolution. The solution is then cooled so that the solution becomes supersaturated to crystalize the desired enantiomer which is isolated. The supersaturated solution is seeded with crystals of the desired enantiomer to increase the enantiomeric excess.

The cooling can be carried out either by a rapid chilling with brine or other refrigerant, or it can be carried out by permitting the vessel containing the solvent and ingredients to set at ordinary room temperatures. The latter form of cooling is preferred in certain embodiments of the present invention, both because of economy in not requiring expensive refrigeration and because good crystal growth and separation from the liquid are obtained.

Once a certain amount of crystallisation has taken place, the crystals are harvested and show a greater weight excess of single desired enantiomer than is represented by the seed crystals. Also, the mother liquors now contain an excess of the enantiomer opposite to that used for the seeding. By recrystallisation of the crystals, a single desired enantiomer hydroxy cineol derivatives (of high optical purity) is obtained in greater amount.

Mother liquors from the procedure containing an excess of one enantiomer can be resubjected to the above procedure but seeding with the opposite enantiomer. By an iterative process of crystallisation (cyclic entrainment), seeding with opposite enantiomers alternately, it is in principle possible to separate an amount of racemic hydroxy cineol derivatives entirely into its enantiomeric components.

Other techniques may be employed to achieve the same separation, such as, for instance, seeding the enantiomeric mixture either in suspension or solution with seeds of both enantiomers but which are of different particle sizes. Then, after crystallisation, the enantiomers may be separated by a size-separation process such as sieving.

In the enrichment procedure of this invention, for crystallisation, a variety of solvents can be chosen and crystallisation can be induced by conventional techniques that obtain a supersaturated solution, such as by cooling of a saturated solution, by solvent evaporation from a saturated solution, or by addition of an additional solvent in which the hydroxy cineol derivatives are less soluble. Suitable solvents for this purpose are, for example, non-polar solvent having polarity index of ≥0.0 to ≤2.5. Preferably, a hydrocarbon having polarity index of ≥0.0 to ≤2.5. More preferably, the hydrocarbon is selected from the group consisting of petroleum ether, pentane, cyclopentane, hexane, cyclohexane, heptane, n-octane, iso-octane, cyclooctane, benzene, xylene and toluene.

The crystals or precipitate formed can be separated from the mother liquor by conventional techniques, such as filtration, vacuum or pressure filtration, centrifugation, and the like. The remaining mother liquor is enriched in the racemate and accordingly provides a source of this enantiomer mixture.

Preferably, the desired enantiomer is isolated by a method selected from the group consisting of filtration or evaporation.

Essentially the desired enantiomer is either the optically active hydroxy cineole derivative of formula (I-R) or the optically active hydroxy cineole derivative of formula (I-S).

Essentially enantiomerically pure hydroxy cineole derivative of the formulae (I-S) and (I-R) should be understood in the context of the present invention to mean that they are present in an enantiomeric purity of in each case at least 98% ee, preferably at least 99% ee and in particular at least 99.5% ee.

The enantiomeric excess of the hydroxy cineole derivative of formulae (I-S) and (I-R) can be determined by means of common processes, for example by determining the optical rotation or by chromatography on a chiral phase, for example by HPLC or gas chromatography using chiral columns.

The remarks made above regarding suitable and preferred embodiments of the invention and of the process apply here correspondingly.

The process according to the presently claimed invention affords the desired enantiomer of cineole derivative in high yields and with a very high enantiomeric purity.

Use of the desired enantiomer of hydroxy cineol derivative of formula (I-R) or formula (I-S) having enantiomeric excess of at least 99.5% ee as prepared according to the invention, is for the synthesis of enantiomerically pure 7-oxabicyclo[2.2.1]heptane derivatives.

Accordingly, enantiomerically pure 7-oxabicyclo[2.2.1]heptane derivatives are selected from the group consisting of (1S,2R,4R)-4-isopropyl-1-methyl-2-(o-tolylmethoxy)-7-oxabicyclo[2.2.1]heptane and (1R,2S,4S)-4-isopropyl-1-methyl-2-(o-tolylmethoxy)-7-oxabicyclo[2.2.1]heptane.

Essentially the mixture of enantiomers of formula (I-R) and formula (I-S) is prepared by metal catalysed epoxidation of a terpinen-4-ol derivative of formula II to obtain an epoxide of formula (III); and subjecting the epoxide of formula (III) to acid catalysed rearrangement.

According to a literature-known procedure (see: Synthetic Communications 1996, 26 (14), 2531-2735) a solution of crude hydroxycineol (chemical purity 67.3% GC-area) in toluene with a enantiomeric ratio of R:S=80:20, was obtained by reacting 1848 g (11 mol) terpinen-4-ol (enantiomeric ratio R:S=80:20) to the corresponding terpinen-4-ol epoxide followed by rearrangement in the presence of sulfuric acid.

The present invention is illustrated by the non-restrictive examples which follow.

Chemicals Used:
1. Terpinen-4-ol (enantiomeric ratio R:S=80:20);
2. Sulfuring acid;
3. Toluene;
4. Petroleum ether;
5. n-pentane;
6. n-hexane;
7. n-heptane;
8. Iso-octane;
9. Cyclohexane;
10. NaOH;
11. $Na_2SO_4$
12. CsCl;
13. Water;
14. Brine;
15. Ethyl acetate;
16. n-heptane; and
17. o-methyl-benzylbromide.

Analytical Methods Used:
A. Optical purity determined by Chiral GC (Standard method using a chiral GC-column like Hydrodex-β-6 TBDM, Macherey & Nagel, 25 m×0.25 mm×0.25 μm);
B. Conversion determined by achiral GC (Standard Method using a GC-column like Chrompack CP Sil-8-CB, Agilent J&W, 30 m×0.32 mm×1 μm); and
C. Optical rotation determined by Polarimeter (Jasco P-1010).

EXAMPLES

Reference Example

A solution of crude hydroxy cineol (chemical purity 67.3% GC-area) in toluene with an enantiomeric ratio of R:S=80:20, was obtained by reacting 1848 g (11 mol) terpinen-4-ol (enantiomeric ratio R:S=80:20) to the corresponding terpinen-4-ol epoxide followed by rearrangement in the presence of sulfuric acid (Ref.: Synthetic Communications 1996, 26 (14), 2531-2735). The solution was evaporated under reduced pressure (60° C.; 100 mbar). The remaining slurry was filtered off and washed with 1 L of −8° C. cold n-heptane. The filter cake was dried under reduced pressure at 40° C.; yielding 488.9 g of hydroxycineol. The chemical purity of the isolated material was 99.9% (by GC); the chiral GC gave an optical purity of 98% ee (R:S=99:1) in favor of the R-enantiomer. The mother liquor of crystallization was cooled to −10° C. and the precipitate was filtered off and washed with 1 L of −20° C. cold n-heptane. After drying under reduced pressure 425.5 g of 99.9% chemical pure hydroxycineol was isolated. The enantiomeric ratio of the second precipitate was R:S=49.7:50.3%.

Example 1

Determination of the solubility of racemic and enantio pure hydroxy-cineol in different solvents. The solubility of racemic hydroxy cineol and enantiopure hydroxy cineol was checked at room temperature in solvents namely, petroleum ether, n-pentane, n-hexane, n-heptane, iso-octane, cyclohexane and toluene.

The solubility at room temperature was determined by adding under stirring small portions of the substance to 5 mL of solvent until it reached saturation and formation of a no more soluble sediment was observed.

TABLE 1

Solubility of racemic hydroxy cineol and enantiopure hydroxy-cineol in different solvents

| solvent | Solubility [g/mL] Racemate | enantiopure material | solubility racemate/ solubilty enantiomer |
|---|---|---|---|
| petroleum ether | 0.12 | 0.02 | 6 |
| n-pentane | 0.15 | 0.03 | 5 |
| n-hexane | 0.1 | 0.02 | 5 |
| n-heptane | 0.08 | 0.01 | 8 |
| iso-octane | 0.075 | 0.02 | 3.8 |
| cyclohexane | 0.38 | 0.07 | 5.4 |
| toluene | 0.8 | 0.26 | 3 |

According to the results, in non-polar solvents the racemic compound is much better soluble than optical pure material. Most preferred is n-heptane, where the racemate is 8-fold better soluble than the optical pure hydroxy-cineol.

Example 2

Separating Enantioenriched R-Enantiomer of 2-hydroxy-1,4-cineole by Lixiviation 3.8 g of enantioenriched 2-hydroxy-1,4-cineole (ee: 50%; R:S=75:25) was stirred at room temperature with n-heptane (22 mL) for 8 hrs. Insoluble material was filtrated, washed with cold n-heptane (3 mL) and dried. 1.85 g of 99% ee (R:S=99.5:0.5) 2-hydroxy-1,4-cineole was obtained as a white powder, m.p.: 89° C.

The filtrates were combined and evacuated to dryness. 1.95 g of almost racemic 2-hydroxy-1,4-cineole (ee=4%; R:S=52:48) were obtained as a white powder, m.p.: 56° C.

Example 3

Separating Enantioenriched S-enantiomer of 2-hydroxy-1,4-cineole by Recrystallization 30.5 g of crude S-2-hydroxy-1,4-cineole (ee: 70%, R:S=15:85) was suspended in n-heptane (125 mL) and heated to reflux. A clear solution was obtained. Upon cooling to room temperature, purified material precipitated as white crystals. The precipitate was filtered of, washed with cold n-heptane (10 mL) and dried, yielding 17.9 g (57%) of pure S-enantiomer (ee: >99%), m.p.: 86° C.

By concentrating the mother liquors, 9 g (30%) of nearly racemic (R:S=45:55) 2-hydroxy-1,4-cineole was obtained as a white solid, m.p.: 55° C.

Example 4

Preparation of Enantiopure Cinmethylin (1R,2S,4S)-Enantiomer (1R,2S,4S)-4-isopropyl-1-methyl-2-(o-tolyl-methoxy)-7-oxabicyclo[2.2.1]heptane

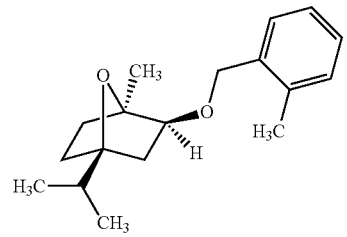 [SMILES: Cc1ccccc1CO[C@H]1C[C@]2(C(C)C)CC[C@@]1(C)O2]

10 g (59 mmol) S-2-hydroxy-1,4-cineole (enantiomeric purity=99.9% ee) according to example 3 was dissolved in toluene (100 mL). Powdered NaOH (3.05 g, 76 mmol) and 0.2 g (1.2 mmol) CsCl was added and the mixture was heated on a Dean-Stark-Trap for 6 hours. Then 10.9 g (60 mmol) of o-methyl-benzylbromide was added dropwise and heating was continued for another 60 hours.

Water (100 mL) was added to the cooled reaction mixture and the phases were separated. The organic layer was extracted twice with brine (20 mL each) and dried over $Na_2SO_4$. The solvent is removed in vacuum to obtain a yellowish oil. The volatile material from the oil was removed in vacuum (bath: 75° C., pressure: 0.1 mbar). The remainder was subjected to column chromatography (eluent: cyclohexane/ethyl acetate 98:2 v/v) yielding a 99.2% pure cinmethylin which was further purified by bulb-to-bulb distillation (0.1 mbar, 135° C.). Finally, 8.5 g (53%) of 1R,2S,4S-cinmethylin with a chemical purity of 99.9% was obtained as a colorless oil.

Optical rotation: [α]D: +58.2° (pure, d=0.99 g/cm³) [α]D: +67.4° (c=5 in ethanol).

Example 5

Preparation of Enantiopure Cinmethylin (1S,2R,4R)-Enantiomer (1S,2R,4R)-4-isopropyl-1-methyl-2-(o-tolyl-methoxy)-7-oxabicyclo[2.2.1]heptane

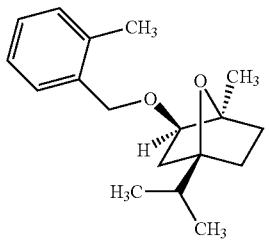 [SMILES: Cc1ccccc1CO[C@@H]1C[C@@]2(C(C)C)CC[C@]1(C)O2]

Following the procedure according to example 4, starting from 10 g (59 mmol) R-2-hydroxy-1,4-cineole (enantiomeric purity=99.9% ee) according to example 2 yielded 7.5 g (46%) of 1S,2R,4R-cinmethylin with a chemical purity of 99.96%.

Optical Rotation:

[α]D: −57.9° (pure, d=0.99 g/cm³) [α]D: −68.5° (c=5 in ethanol).

The invention claimed is:

1. A method for separating an optically active hydroxy cineole derivative of formula (I-R),

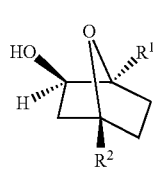

formula (I-R)

or an optically active hydroxy cineole derivative of formula (I-S),

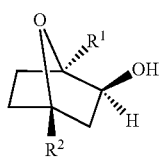

formula (I-S)

wherein
R¹ is methyl and
R² is isopropyl;
from a mixture comprising the enantiomers of formula (I-R) and formula (I-S), the method comprising the steps of:
i) Providing a suspension comprising a mixture of the enantiomers of formula (I-R) and formula (I-S), wherein the desired enantiomer is present in the mixture in an amount of ≥51 to ≤95 wt.-%, related to the sum of the enantiomers of the mixture, in at least one non-polar solvent;
ii) Separating the desired enantiomer by lixiviation consisting of stirring the suspension obtained in step (i) at temperature in the range of ≥10° C. to reflux temperature of the non-polar solvent such that the desired enantiomer is separated from soluble substances, wherein the desired enantiomer is present as an insoluble material; and
iii) Isolating the desired enantiomer obtained in step (ii) by filtration.

2. The method of claim 1, wherein the desired enantiomer is either the optically active hydroxy cineole derivative of formula (I-R) or the optically active hydroxy cineole derivative of formula (I-S).

3. The method of claim 1, wherein in step (ii) the suspension is stirred at temperature in the range of ≥10 to ≤120° C.

4. The method of claim 1, wherein in step (iii) the desired enantiomer as isolated has enantiomeric excess of at least 99.5% ee.

5. The method of claim 1, wherein in step (i) the non-polar solvent is a hydrocarbon.

6. The method of claim 5, wherein in step (i) the non-polar solvent is the hydrocarbon having polarity index of ≥0.0 to ≤2.5.

7. The method of claim 6, wherein the hydrocarbon is selected from the group consisting of petroleum ether, pentane, cyclopentane, hexane, cyclohexane, heptane, n-octane, iso-octane, cyclooctane, benzene, xylene and toluene.

8. The method of claim 1, wherein the mixture of enantiomers of formula (I-R) and formula (I-S) is prepared by a process comprising the steps of:
(iv) epoxidation of a terpinen-4-ol derivative of formula II

Formula (II)

wherein
R¹ is methyl and
R² is isopropyl;
in the presence of at least one metal to obtain an epoxide of formula (III);

Formula (III)

wherein R¹ and R² are defined as above,
and
(v) subjecting the epoxide of formula (III) to at least one acid.

* * * * *